United States Patent [19]

Cosyns et al.

[11] 4,230,897

[45] Oct. 28, 1980

[54] PROCESS FOR SELECTIVELY HYDROGENATING A HYDROCARBON CUT CONTAINING AT LEAST ONE DIOLEFINIC HYDROCARBON AND AT LEAST ONE ACETYLENIC HYDROCARBON USING A PALLADIUM CATALYST WITH CRYSTALLITES OF AT LEAST 50 ANGSTROMS

[75] Inventors: Jean Cosyns, Maule; Robert Stern, Paris; Jean-François Le Page, Rueil Malmaison, all of France

[73] Assignee: Institut Francais du Petrole, Rueil-Malmaison, France

[21] Appl. No.: 26,984

[22] Filed: Apr. 4, 1979

[30] Foreign Application Priority Data

May 5, 1978 [FR] France ............................. 78 10490

[51] Int. Cl.$^3$ ............................. C07C 5/08; C07C 7/00
[52] U.S. Cl. ................................ 585/260; 585/265; 585/850; 585/852; 252/466 PT
[58] Field of Search ............... 585/260, 265, 850, 852; 252/466 PT

[56] References Cited

U.S. PATENT DOCUMENTS

| 3,116,342 | 12/1963 | Robinson et al. | 585/260 |
| 3,898,298 | 8/1975 | Desiderio et al. | 585/265 |
| 3,969,267 | 7/1976 | McVicker | 252/466 PT |
| 4,093,643 | 6/1978 | Vannice et al. | 252/466 PT |

FOREIGN PATENT DOCUMENTS

| 832200 | 4/1960 | United Kingdom | 252/466 PT |
| 1175148 | 12/1969 | United Kingdom | 252/466 PT |

*Primary Examiner*—Veronica O'Keefe
*Attorney, Agent, or Firm*—Millen & White

[57] ABSTRACT

Process for selectively hydrogenating acetylenic hydrocarbons such as vinylacetylene contained in an unsaturated hydrocarbon fraction such as a $C_4$ fraction also containing a diolefinic hydrocarbon such as butadiene, without substantially hydrogenating said diolefinic hydrocarbon, comprising the step of contacting said fraction, at least partially in the liquid phase, in the presence of hydrogen, with a catalyst of palladium on alumina whose palladium crystallites have an average size of at least 50 Angströms, said step being optionally followed with a step of contacting the resultant fraction from the preceding step, in the presence of hydrogen, with a catalyst of palladium an alumina whose palladium crystallites have an average size of at most 45 Angströms.

16 Claims, No Drawings

PROCESS FOR SELECTIVELY HYDROGENATING A HYDROCARBON CUT CONTAINING AT LEAST ONE DIOLEFINIC HYDROCARBON AND AT LEAST ONE ACETYLENIC HYDROCARBON USING A PALLADIUM CATALYST WITH CRYSTALLITES OF AT LEAST 50 ANGSTROMS

This invention concerns a process for the selective hydrogenation of acetylenic hydrocarbons contained in a mixture of hydrocarbons comprising diolefinic hydrocarbons.

The processes for converting hydrocarbons at high temperatures, such for example as steam-cracking, produce unsaturated hydrocarbons, for example, ethylene, propylene, butadiene and butenes, and hydrocarbons having a boiling point in the gasoline range; the gaseous olefinic and diolefinic hydrocarbons of 2 to 4 carbon atoms, obtained by this process, also contain a certain amount of acetylenic hydrocarbons. The content of these hydrocarbons varies in accordance with the severity of the conversion treatment but is always too low for justifying their separation and their use as such in the petrochemical field. However, their presence, together with olefinic and diolefinic hydrocarbons, makes it difficult or even impossible to use the latter in the petrochemical field. This is, for example, the case of butadiene from which vinylacetylene and butynes must be removed to the largest possible extent in order to make the butadiene suitable for the production of elastomers.

For removing these acetylenic hydrocarbons, it has been proposed, in various prior processes, to separate, for example by extractive distillation, hydrocarbons of different unsaturation degrees. Thus, for example in the case of the $C_4$ cut it is possible to separate the saturated compounds having 4 carbon atoms, the butenes, butadiene and the acetylenic compounds. However, in order to obtain the desired purity, these processes require expensive equipment and, moreover, have the disadvantage of resulting in a loss of yield due to the fact that the resulting hydrocarbon cut, at a very high concentration of acetylenic compounds, cannot be used in the petrochemical field.

Other processes have been proposed to avoid these disadvantages; for the most part, they consist of selectively hydrogenating the acetylenic compounds contained in the charge, for example a raw $C_4$ fraction from steam-cracking. A typical charge contains, for example, from 20 to 50% of butadiene, from 40 to 80% of butane, butenes and/or isobutene and from 0.1 to 0.5% of acetylenic compounds comprising, for example, from 0.05 to 0.2% of butyne and from 0.1 to 0.4% of vinylacetylene. The increasing severity of steam-cracking (increase of the furnace temperature) gave rise, these last years, to cuts having much higher contents of acetylenic compounds, often equal to or higher than 1% by weight, for example from 0.2 to 0.5% by weight of butynes and from 1 to 3% by weight of vinylacetylene.

Such contents of acetylenic hydrocarbons pose new problems for the hydrogenation processes, particularly the problem of the rapid deactivation of the catalyst due to the formation and to the deposit of polymers as well as that of a progressive dissolution of the active metal, which is the more substantial as the acetylenic hydrocarbon content is higher.

The problem of preparing catalysts which are stable in these reactions is not simple. For example, the French patent specification No. 1 502 462 shows that, even in the case of a charge of relatively low content of acetylenic hydrocarbons, a catalyst of palladium on calcined alumina has already lost a large part of its activity and selectivity after only 7 days of use.

The present invention has for an object the avoidance of these drawbacks; it is a particular object to propose the use of catalysts having an initial activity substantially equal or slightly lower than that obtained with the palladium catalysts of a known type, but which remain much more stable over a long period. Furthermore, in these catalysts, the palladium content does not change substantially during time, even with charges of high acetylenic hydrocarbon content.

The process according to the invention comprises hydrogenating the cut to be treated, at least partially in liquid phase, over a supported palladium catalyst whose crystallite average size is at least 50 Angströms. This size can be measured, for example, by electron microscopy. A catalyst conforming with this definition may be prepared by incorporating a palladium compound to alumina in a proportion of from 0.1 to 5% by weight of palladium with respect to the carrier, followed with activation by heating at a temperature from 600° to 1100° C., preferably from 700° to 950° C., said heating being optionally conducted in neutral atmosphere, for example nitrogen, or reducing atmosphere, for example hydrogen, or oxidizing atmosphere, for example a free oxygen containing gas. It is however preferable to proceed in an oxidizing atmosphere which provides for a particularly rapid formation of palladium crystallites. The process can be conducted at any pressure, for example at normal pressure. It is possible, if necessary, to proceed with a final reduction step, for example by means of hydrogen, according to a known technique, the reduction temperature being preferably from 0° to 200° C.

The activation by heating may be performed, for example, over 0.2 to 24 hours, the reduction time being itself, for example, from 0.2 to 24 hours. The reduction is preferably performed in the hydrogenation reactor, either before or at the beginning of a hydrogenation operation.

The carrier is preferably alumina of an initial specific surface (before incorporation of palladium and activation) lower than 100 $m^2/g$, for example from 1 to 100 $m^2/g$.

The method for incorporating the palladium compound is not critical; for example, it is possible to mix the components in the dry state or in the presence of water or to impregnate the carrier by means of a solution of a palladium compound. The palladium compound may be any of the palladium compounds known or proposed for a similar use, for example palladium nitrate, palladium chloride or palladium acetyl acetonate. In some cases, other metals having a co-catalytic effect may be added.

The use of lower activation temperatures leads to the formation of catalysts whose average size of the crystallites is below 45 Å; these catalysts are not stable enough.

The preferred operating conditions are as follows:
Total pressure: 1 to 50 bars and preferably 3 to 10 bars
Space velocity: 1 to 50 and preferably 10 to 50 (liquid charge volume/catalyst volume/hour)
Temperature: 0° to 100° C. and preferably 10° to 50° C.

Ratio H$_2$/acetylenic compounds expressed in moles by mole: 1 to 5 and preferably 1.1 to 2.

According to an alternative embodiment, whereby it is possible to proceed with a high initial activity, without substantial loss of palladium, the hydrocarbon charge and hydrogen are first passed over the abovementioned catalyst having crystallites of at least 50 Å, and then over a conventional catalyst of palladium on alumina, whose palladium crystallites have an average size of at most 45 Å.

As above indicated, it is necessary, for obtaining a catalyst with small crystallites, to proceed to a calcination at a relatively low temperature, lower than 600° C., for example from 300° to 550° C., in neutral, reducing or oxidizing atmosphere: the calcination time is, for example, from 0.2 to 24 hours.

For other details of the preparation of the catalyst with small crystallites, referred to the above mentioned prior art. In particular, a calcination under neutral or oxidizing atmosphere is advantageously followed with a reduction by means of hydrogen, for example at 0°-200° C., this reduction step being optionally performed directly in the hydrogenation reactor, either before or at the beginning of the hydrogenation operation. There is advantageously used from 5 to 70%, preferably from 20 to 60% by volume of catalyst having large crystallites (first catalyst) with respect to the total volume of the the two catalysts.

The conversion of the acetylenic hydrocarbons may conveniently be deduced from the conversion of vinylacetylene, in the case of a C$_4$ cut containing both butadiene and acetylenic hydrocarbons. It is then advantageous to convert from 50 to 90%, preferably from 60 to 85%, of the vinylacetylene in contact with the first catalyst and to continue the reaction, for example up to a conversion rate of 94% or more of the vinylacetylene, in contact with the second catalyst.

EXAMPLE 1 (comparative)

A catalyst is prepared by impregnating, with a nitric solution of palladium nitrate, an alumina carrier, consisting of balls of a 2 mm diameter, having a specific surface of 57 m$^2$/g and a total pore volume of 0.6 cc/g, so as to obtain a final catalyst having a palladium content of 0.2% by weight. After impregnation, the catalyst is dried at 120° C. in a drying oven and roasted at 450° C. for 2 hours in an air stream.

A sample of the catalyst is reduced by passing a hydrogen stream at 100° C. for 2 hours; it is then examined by electron microscopy. It is found that the average size of the palladium crystallites is 35 Å. The catalyst is charged into a tubular reactor and reduced in situ by means of a hydrogen stream at 100° C. for 2 hours.

The charge to be treated has the following composition:

| Compound | % mole |
|---|---|
| Isobutane | 0.21 |
| Propylene | 0.05 |
| n butane | 0.53 |
| 1-butene | 12.70 |
| Isobutene | 19.30 |
| 2-butene trans | 4.18 |
| 2-butene cis | 3.30 |
| 1,3-butadiene | 57.62 |
| 1,2-butadiene | 0.25 |
| 1-butyne | 0.21 |
| Vinylacetylene | 1.65 |
| Total : | 100 |

The operating conditions are as follows:
Space velocity: 10
Total pressure: 8 bars
Temperature: 40° C.
Ratio H$_2$/acetylenic compounds: 1.2 mole/mole The results obtained, in relation with the duration of the test, are summarized in Table I.

TABLE I

| TIME IN HOURS | CONVERSION of vinylacetylene in % | CONVERSION of 1-butyne in % | R$_{1,3\text{-}BD}$* in % |
|---|---|---|---|
| 50 | 98 | 76 | 97.5 |
| 140 | 94 | 55 | 98.9 |
| 720 | 85 | 36.5 | 99.7 |

*R$_{1,3\text{-}BD}$ in % = yield of 1,3-butadiene,
i.e. : $\frac{\% \text{ BD in the product}}{\% \text{ BD in the charge}} \times 100$ It is essentially desired to obtain a conversion of vinylacetylene of at least 94%, which corresponds to a final product containing less than 1000 ppm of vinylacetylene. It is clear from Table I that such performance is attained over only 140 hours. However the test has been continued up to 720 hours.

The catalyst is then withdrawn from the reactor and it is observed that it contains no more than 0.1% by weight of palladium instead of the initial 0.2%. Moreover, it contains about 4.6% by weight of carbon resulting from polymer deposits.

EXAMPLE 2 (conforming with the invention)

As in example 1, there is prepared a catalyst containing, in its final state, 0.2% by weight of palladium. The catalyst is dried as in example 1 but is roasted under different conditions, i.e. at 900° C. for 2 hours.

A sample of the catalyst is examined by electron microscopy; after reduction in a hydrogen stream at 100° C. for 2 hours, the average crystallite diameter is found to be 80 Å. The catalyst is charged into a reactor and reduced as in example 1. The charge to be treated is the same as in example 1.

The results obtained with this catalyst are summarized in Table II.

TABLE II

| TIME IN HOURS | CONVERSION of vinylacetylene in % | CONVERSION of 1-butyne in % | R$_{1,3\text{-}BD}$ in % |
|---|---|---|---|
| 50 | 95 | 60 | 97.5 |
| 720 | 94.5 | 59 | 98.0 |

It is observed that the catalyst according to the invention, although initially less active, substantially maintains its activity over the whole test period.

The catalyst withdrawn from the reactor contains 0.195% by weight of palladium in proportion to the alumina, which corresponds substantially to the starting concentration. The exhausted catalyst contains about 3% by weight of deposits, expressed as carbon.

EXAMPLE 3 (conforming with the invention)

The C$_4$ cut whose composition is given in example 1 is treated in a reactor containing two successive catalyst beds: the first bed, amounting to 50% of the total volume of the catalyst, consists of the catalyst of example 2 having palladium crystallites of 80 Å on alumina, whereas the second bed, amounting to 50% of the total volume of the catalyst, consists of the catalyst of example 1 having palladium crystallites of 35 Å on alumina.

The operating conditions are as follows:
Hourly space velocity: 10 volumes of liquid $C_4$ cut per volume of catalyst
Total pressure: 8 bars
Temperature: 40° C.
Ratio $H_2$/acetylenic hydrocarbons: 2 moles/mole Hydrogen is distributed as follows: 55% at the inlet of the first bed and 45% at the inlet of the second bed.

The results are as follows:

| TIME IN HOURS | OUTLET from FIRST CATALYST BED | | | OUTLET from SECOND CATALYST BED | | |
|---|---|---|---|---|---|---|
| | Residual VAC ppm (1) | VAC conversion % | R (2) | Residual VAC ppm (1) | VAC conversion % | R (2) |
| 50 | 2900 | 82.4 | 93.85 | 90 | 99.45 | 96.4 |
| 720 | 3000 | 81.8 | 99 | 95 | 99.40 | 96.5 |

(1) - VAC = vinylacetylene (2) - Yield of 1,3-butadiene : $R = \frac{\% \text{ BD in the product}}{\% \text{ BD in the charge}} \times 100$ The results show that the conversion of vinylacetylene remains substantially constant and that there is obtained a high yield of butadiene.

After 720 hours of run, the two catalysts are analysed: the first catalyst contains 0.196% by weight of palladium and the second one 0.198% by weight of palladium. No substantial entrainment of palladium is thus observed.

EXAMPLE 4 (comparative)

Example 3 is repeated, under unchanged conditions, except that the catalyst in the two beds consists of a palladium catalyst hanving crystallites of 35 Å.

The following results are obtained:

| TIME in HOURS | Residual VAC ppm | VAC conversion in % | R |
|---|---|---|---|
| 50 | 50 | 99.7 | 96.2 |
| 150 | 297 | 98.2 | 97.3 |
| 720 | 940 | 94.3 | 98.3 |

There is observed a progressive deactivation of the catalyst. After 720 hours of operation, the analysis of the catalyst shows that it contains no more than 0.12% by weight of palladium instead of the initial 0.2%.

EXAMPLE 5 (comparative)

Example 3 is repeated under the same conditions except that the catalyst in the two beds consists of a palladium catalyst having crystallites of 80 Å.

The following results are obtained:

| TIME in HOURS | Residual VAC ppm | VAC conversion in % | R |
|---|---|---|---|
| 50 | 120 | 99.3 | 93.9 |

-continued

| TIME in HOURS | Residual VAC ppm | VAC conversion in % | R |
|---|---|---|---|
| 720 | 130 | 99.2 | 94 |

It is apparent that the catalyst was substantially not deactivated. The analysis after 720 hours shows that it still contains 0.195% by weight of palladium, i.e. substantially the same content as that of the fresh catalyst.

The activity is lower (120 to 130 ppm of residual VAC instead of 90 to 95 ppm) and the butadiene yield is also lower (about 94% instead of about 96.5%).

What we claim is:

1. In a process for selectively hydrogenating a hydrocarbon fraction containing simultaneously at least one diolefinic hydrocarbon and at least one acetylenic hydrocarbon, including the hydrogenation of the acetylenic hydrocarbon but without substantial hydrogenation of the diolefinic hydrocarbon, wherein said fraction, at least partially in the liquid phase, and hydrogen are contacted with a catalyst of palladium on alumina, the improvement wherein the average size of the palladium crystallites in said catalyst is of at least 50 Angstroms, whereby the selective hydrogenating activity of the catalyst is substantially prolonged.

2. A process according to claim 1, wherein the hydrocarbon fraction is an unsaturated $C_4$ fraction containing butadiene and vinylacetylene.

3. A process according to claim 1, wherein the hydrocarbon fraction contains from 20 to 50% by weight of butadiene, from 40 to 80% by weight of butane, butenes and/or isobutene and at least 1% by weight of acetylenic hydrocarbons.

4. A process according to claim 1, wherein the catalyst is obtained by admixing alumina with at least one palladium compound and subsequently heating at a temperature from 650° to 1100° C.

5. A process according to claim 4, wherein the heating is conducted at 750°–950° C.

6. A process according to claim 4, wherein the heating is conducted in a free oxygen containing atmosphere.

7. A process according to one of claim 4, wherein the heating is followed with a reduction treatment with hydrogen.

8. A process according to claim 1 wherein after having been contacted with the catalyst in a catalyst bed whose average palladium crystallite size is of at least 50 Angstroms, the hydrocarbon fraction and hydrogen are contacted in a further catalyst bed having a catalyst of palladium on alumina whose palladium crystallites have an average size of at most 45 Angstroms.

9. A process according to claim 8 wherein from 5 to 70% of the total volume of the two catalyst beds correspond to the catalyst bed having an average size of the crystallites of at least 50 Angstroms.

10. A process according to claim 8, wherein from 10 to 50% of the total volume of the two catalyst beds correspond to the catalyst bed having an average size of the crystallites of at least 50 Angstroms.

11. A process according to claim 8, wherein a hydrocarbon $C_4$ cut containing simultaneously butadiene and acetylenic hydrocarbons is treated under such operating conditions as to convert from 50 to 90% of the vinylacetylene in contact with the first catalyst bed and then to proceed to a further conversion of the vinylacetylene up to 94% or more, in contact with the second catalyst bed.

12. A process according to claim 11, wherein 60–85% of the vinylacetylene is converted in contact with the first catalyst bed.

13. A process according to claim 1, wherein the average size of the palladium crystallites is about 80 Angströms.

14. A process according to claim 11, wherein the average size of the palladium crystallites in the first mentioned catalyst bed is about 80 Angströms, and the average size of the palladium crystallites in the second mentioned catalyst bed is about 35 Angströms.

15. The process of claim 1, wherein the acetylenic hydrocarbon content is at least 1% by weight.

16. The process of claim 4, wherein alumina has a specific surface from 1 to 100 $m^2/g$.

* * * * *